(12) United States Patent
Babaev

(10) Patent No.: US 8,376,969 B2
(45) Date of Patent: Feb. 19, 2013

(54) METHODS FOR TREATMENT OF SPIDER VEINS

(75) Inventor: Eilaz Babaev, Minnetonka, MN (US)

(73) Assignee: Bacoustics, LLC

( * ) Notice: Subject to any disclaimer, the term of this patent is extended or adjusted under 35 U.S.C. 154(b) by 637 days.

(21) Appl. No.: 12/234,755

(22) Filed: Sep. 22, 2008

(65) Prior Publication Data

US 2010/0076350 A1   Mar. 25, 2010

(51) Int. Cl.
*A61H 1/00* (2006.01)

(52) U.S. Cl. .................................. 601/2; 601/3

(58) Field of Classification Search .............. 600/407, 600/437, 471; 604/509; 607/96, 50, 104; 601/2
See application file for complete search history.

(56) References Cited

U.S. PATENT DOCUMENTS

| 7,232,431 | B1 * | 6/2007 | Weimann | 604/500 |
| 2002/0190136 | A1 * | 12/2002 | Babaev | 239/102.2 |
| 2003/0229304 | A1 * | 12/2003 | Babaev | 604/22 |
| 2004/0106867 | A1 * | 6/2004 | Eshel et al. | 600/439 |
| 2005/0209580 | A1 * | 9/2005 | Freyman | 604/509 |
| 2006/0079868 | A1 * | 4/2006 | Makin et al. | 606/27 |
| 2007/0088217 | A1 * | 4/2007 | Babaev | 600/471 |
| 2009/0053397 | A1 * | 2/2009 | Buchner et al. | 427/74 |

* cited by examiner

*Primary Examiner* — Tse Chen
*Assistant Examiner* — Joel F Brutus

(57) ABSTRACT

A medical ultrasound apparatus and associated methods of use is disclosed enabling a relatively non-invasive or minimally invasive method to treat skin or tissue. The apparatus is constructed from an ultrasound tip mechanically coupled to a shaft. The shaft is mechanical coupled to an ultrasound transducer driven by an ultrasound generator. The ultrasound tip possesses at least one radial surface, a cavity, or some other form of a hollowed out area, within at least one of the radial surfaces, and a non-metallic sheath covering portions of the tip so that only the sheath and not the tip would normally contact the patient's skin. The disclosed method of treating spider, reticular or small varicose veins with the apparatus can be practiced by contacting the sheath with the patient's epidermal skin layers and delivering ultrasonic energy released from the various surfaces of the vibrating tip to the skin and/or tissue through direct contact and/or with a coupling fluid focused from a cavity.

13 Claims, 3 Drawing Sheets

METHODS FOR TREATMENT OF SPIDER VEINS

BACKGROUND OF THE INVENTION

Varicose veins are blood vessels that have become twisted and swollen when their one-way valves are compromised or when the vein wall weakens. Spider veins are those thin networks of vessels that appear on the skin. As people grow older, the likelihood of having large and/or smaller varicose and spider veins increases. In fact, varicose and spider veins affect over half the population by age 55 and are linked to factors such as heredity, pregnancy, estrogen medications, prolonged standing or sitting, sedentary lifestyle, and injury to the legs. Left untreated, varicose veins can cause pain, swelling, phlebitis, chronic skin ulcers, and potentially life-threatening blood clots.

Spider veins often appear on the skin of the lower extremities. These are abnormally dilated segments of the normal network of small veins in the skin. There is a significant genetic or hereditary predisposition to developing these abnormal vessels. In addition, progesterone stimulates the development of these abnormal veins. As a result these are more commonly seen in women, and may develop in association with pregnancy. Spider veins, although not usually symptomatic, occasionally they can be painful.

Though often benign, many individuals desire treatment of spider veins because of their appearance. Sclerotherapy, laser and intense-pulsed-light therapy, radio-frequency ablation, and medical extirpation are the techniques typically used to ablate varicosities.

During sclerotherapy a sclerosing agent such as polidocanol or hypertonic sodium chloride is injected in the dilated vein. A high degree of skill is required for this procedure. The treatment is ineffective in cases where a deeper aberrant vein is missed. Further, the technique has significant morbidity in cases where the agent extravasates outside the blood vessel. Microsclerotherapy is a type of sclerotherapy that uses improved solutions and injection techniques that increase the success rate for removal of spider veins.

In one type of ablation procedure, the surgeon inserts a very thin catheter into the enlarged vein and applies heat through the tip of the catheter. When the catheter is withdrawn, the heat causes the vein to collapse and the blood to reroute through healthier veins. Catheter assisted methods can use radio waves or lasers to close the main vein or a mechanical blade to remove the branch varicose veins.

SUMMARY OF THE INVENTION

This disclosure is for a method and apparatus using ultrasound energy capable of providing a non-invasive or minimally invasive therapeutic effect. The method and apparatus may be used to treat vascular malformations and/or other vascular disorders in the dermis and/or subcutaneous layers of the skin. The disclosed method and apparatus may have other uses. By way of example, the method and apparatus will be described with reference to the treatment of spider veins.

The method and apparatus are capable of providing a minimally invasive and/or non-invasive treatment of spider veins. When used under non-invasive conditions, spider veins can be treated without breaking the skin. Therefore, in addition to its use by physicians, the disclosed device may also be useable by non-physicians such as physical therapists and other medical specialists that are restricted from using devices capable of breaking the skin.

With the present invention, the apparatus comprises an ultrasound generator driving an ultrasound transducer. An ultrasound horn is mechanically coupled to the ultrasound transducer. The ultrasound horn consists of a shaft and an ultrasound tip. The ultrasound horn receives the ultrasound waves from the ultrasound generator and transmits the ultrasound waves to the distal end of the ultrasound tip. The shaft and the ultrasound tip may be integral parts or may be mechanically coupled. The ultrasound tip comprises at least one radial surface, a cavity or some other form of a hollowed out area within at least one of the radial surfaces, and a radial edge circumventing the opening of the cavity. In a preferred embodiment, a tapered edge or point is provided to concentrate vibrations passing through the tip. A coupling fluid is used to enhance transmission of ultrasound waves from the cavity.

In one embodiment, a transducer is configured to deliver ultrasound energy to the regions of the superficial tissue (e.g., skin) such that the energy is deposited at the particular depth at which the vascular malformations are located below the skin surface. The ultrasound transducer can be driven at different frequency regimes such that the depth and shape of energy concentration can match the region of treatment.

The ultrasound tip adjoins a non-metallic sheath preventing concentrating elements on the tip from contacting the patient's skin. The sheath is preferably made of a flexible removable material such as rubber, plastic, fluoropolymer or other polymer. The material is chosen so that it is sufficiently elastic so that; 1) it may be installed over the wide portions of the ultrasound tip, 2) once installed it will attach to the ultrasound tip so it will not be dislodged during use, and 3) it may be easily replaced after each use. The sheath may be constructed of a segmented design to facilitate installation and removal of the shield. An example of this would be having the segments substantially independent with one or more points of attachment for the segments, such as the petals of a flower. A lubricant or gel such as silicone based materials may be used to displace air between the shield and the ultrasound tip to modify the ultrasound transmission characteristics to the patient's skin.

Alternatively, the sheath may be a reusable permanent polymer coating such as fluropolymer, epoxy or a plastic polymer integrally deposited over the ultrasound tip that is cleaned after each use. In either embodiment, the sheath prevents the metal surfaces and edges of the tip from contacting the patent's skin and potentially breaking the skin layer. This allows the device and method to be used by physical therapists and other medical personnel that would not be certified to use a device capable of breaking the skin layer during use.

Ultrasound may be applied to the skin and underlying tissues by at least two mechanisms. The sheath may be contacted to the skin allowing ultrasound energy to be transferred directly from the device, such as from a radial surface or radial edge. In addition, the ultrasound energy may be focused by the cavity of the radial surface to the skin. In this case, the coupling fluid serves as a transfer medium to allow transfer of the ultrasound waves to the skin surface to greatly enhance the ultrasound transfer efficiency across the air interface. Typically, the focal point of the cavity is at or below the skin layer so that the therapeutic effect of the ultrasound is directed to treating the vascular tissue causing spider veins which are generally located just below the skin surface.

Ultrasound energy may be optimized to achieve the desired effects by effectively utilizing its various properties including; thermal treatment, cavitation, microstreaming and harmonic resonance. At higher intensities, the use of the thermal energy produced from the ultrasound waves and the focused cavitation and microstreaming effects are particularly effective at disrupting or destroying unwanted tissue such as the vascular tissue of spider veins. Focusing the ultrasound allows precise placement and control of the levels of energy released from cavitation and microstreaming. Specifically, the concentrated ultrasound waves from the concentrating elements on the edge circumventing the cavity may collapse the vein which is then ablated/disrupted by the focused ultrasound energy emanating from the walls of the cavity. Before, after and/or during the treatment of spider veins the operating parameters may be altered to achieve additional therapeutic effects. For example, the intensity of ultrasound may be increased and/or the focus shifted away from the blood vessels being treated as to induce cavitations and/or microstreaming capable of inducing the ablation of tissue at a secondary site. In combination or in the alternative, the intensity of the ultrasound energy could be lowered as to aid in the facilitation of angiogenesis. In combination with or in the alternative to adjusting the intensity of the ultrasound delivered, the frequency and/or amplitude of the ultrasound may be adjusted as to correspond with the harmonic resonance of different tissues as to optimize the interaction with the tissue.

DETAILED DESCRIPTION OF THE INVENTION

Figure 1:
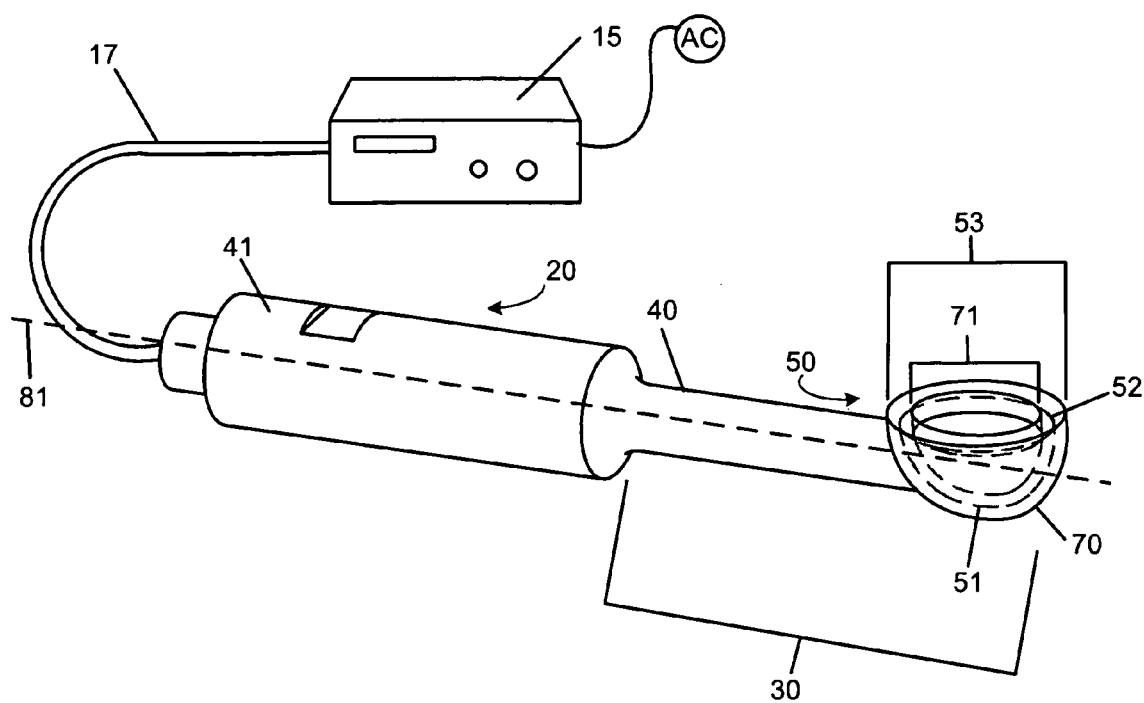
FIG. 1 is a perspective view of one embodiment of the medical apparatus with a disposableسheath.

The present invention is an ultrasound medical method and device capable of providing for the relatively non-invasive or minimally invasive treatment of spider veins, skin or other tissue treatment. FIG. 1 depicts one possible embodiment of the ultrasound medical apparatus of the present invention. The depicted embodiment of the present invention comprises an ultrasound generator 15 with an electrical cord supplying the ultrasound generator 15 its power, such as standard AC or battery power. The ultrasound generator 15 is in electrical communication with an ultrasound transducer 20 through a signal connector 17. A hand piece contains the ultrasound transducer 20 driven by the ultrasound generator 15, a housing surrounding the ultrasound transducer 20 provides a gripping surface and may cover portions of an ultrasound horn 30 connected to the distal end of the ultrasound transducer 20.

Ultrasound generator 15 and ultrasound transducer 20 are well known in the art and will not be described in detail herein. However, control of the electrical signal directly influences the ultrasound wave properties and allows optimization of the ultrasound treatment particularly with respect to the ultrasound thermal, cavitation and microstreaming properties. The ultrasound generator 15 should be capable of producing an electrical signal of a sufficient alternating voltage to drive the ultrasound transducer 20 and to achieve the desired therapeutic effect. The ultrasound transducer 20 converts the alternating voltage into mechanical motion as to induce a shaft 40 to vibrate. The shaft 40 transmits the ultrasonic vibrations to the ultrasound tip 50 to induce vibrations. Preferably the ultrasound tip 50 is induced to vibrate approximately in resonance with the ultrasound waves to carry the ultrasound energy. The amplitude of the vibrations produced may be any in the ultrasound spectrum, but are typically between approximately 1 micron and approximately 300 microns. The preferred amplitude range is approximately 60 microns-100 microns. The recommended amplitude value is approximately 80 microns.

For treatment of spider veins and other tissue and/or skin disorders, the electrical signal produced by ultrasound generator 15 should also be sufficient to drive the ultrasound transducer 20 to induce the ultrasound tip 50 to vibrate approximately in resonance at any frequency within the ultrasound spectrum, such as, but not limited to, between approximately 15 kHz and approximately 3 mHz. The preferred frequency range for the ultrasound tip 50 is 15 kHz to 50 kHz with a recommenced frequency of approximately 30 kHz. The ultrasound generator 15 may have multi-frequency capabilities to operate at selectable alternative frequencies.

Ultrasound transducer 20 may be driven with a continuous wave or pulsed frequency signal supplied by ultrasound generator 15. Driving transducer 20 with a continuous wave tends to induce the release of standing waves from the various surfaces of tip 50, while a pulsed frequency reduces or avoids the release of standing waves. The pulsed frequency signal generates less heat, cavitation and streaming currents, and may increase the longitudinal force of the induced vibrations as a result of the on/off cycle changes. The electrical signal may be changed depending on the desired features of the released ultrasound waves for the particular application. For example, inducing the release of standing waves may be helpful to produce or increase cavitation effects. The wave form of the electrical signal may be sinusoidal, rectangular, trapezoidal and/or triangular. In addition, the electrical signal from the ultrasound generator 15 may be fixed or modulated to allow ultrasonic wave amplitude variability. Ultrasound generator 15 may include feedback control to adjust the signal.

The ultrasound energy selected to penetrate to the subcutaneous tissue layer of the skin is generally applied for a duration of time from about 1 millisecond to about 30 minutes, such that the ultrasonic radiation damages the subcutaneous tissue, and allows for the natural re-growth of new cellular structure.

A housing serving as a handle for the ultrasound device may isolate the ultrasound transducer 20 from the device operator. Operators of the ultrasound device can hold the housing during use to manipulate the device. The housing provides a surface appropriate for hand manipulation by the therapist and/or user while allowing the user to avoid direct contact with vibrations within the device. The housing may extend over the entire ultrasound transducer 20 and/or may partially enclose portions of the shaft 40.

The ultrasound horn 30 may include a shaft 40 and an ultrasound tip 50 all driven by the ultrasound transducer 20. The shaft 40 may be mechanically coupled to an ultrasound tip 50. The shaft 40 and ultrasound tip 50 connections may be completed by threading, welding and/or other means readily recognizable by people of ordinary skill in the art. The ultrasound tip 50, or portions of the ultrasound tip 50, may be removable from the hand piece for cleaning, sterilization and/or replacement as would be understood by those skilled in the art upon review of this disclosure. The shaft 40 and ultrasound tip 50 may be fabricated from metals such as, but not limited to, alloys of titanium, aluminum and/or steel.

The shaft 40 portion of the ultrasound tip 50 may have a longitudinal axis 81. The ultrasound horn 30 comprises at least one radial surface 51, a cavity 53 or some other form of a hollowed out area within at least one of the radial surfaces 51, and a radial edge 52 circumventing the opening of the cavity 53. The radial edge 52 may have a tapered edge or at least one point to concentrate energy release along the radial edge 52. The ultrasound tip 50 adjoins a non-metallic sheath 70 covering those portions of the tip that would otherwise contact the patient's skin. Alternatively the sheath 70 may extend past the concentrating elements to provide a gap between the concentrating element and the patient's skin. Therefore during normal use, the sheath 70 prevents the metal surfaces and edges of the tip 50 from contacting the patent's skin and potentially breaking the skin layer. In this embodiment, the sheath 70 does not need to cover all or any of the radial edge 50. It is sufficient for the sheath 70 to maintain separation between the ultrasound tip 50 and the patient's skin. For example, the sheath 70 may simply extend beyond the lip of the radial edge 50 without actually covering it. The sheath 70 allows use of the device and method to be used by physical therapists and other medical personnel that would not be certified to use a device that could otherwise break the patient's skin layer.

The sheath 70 has an aperture 71 approximating the interior circumference of the radial edge 52 and is designed to at least cover portions of the radial edge 52 to prevent contact between the metal surfaces of the ultrasound tip 50 and the patient's skin. A lubricant such as water, mineral oil or silicone gel which may be used to fill any space between the ultrasound tip 50 and the sheath 70 to improve ultrasound transmissions to the patient's skin. The disposable sheath 70 may be constructed of a plastic or polymer which may be formed in sections that may be releasably assembled to cover portions of the ultrasound tip. In another embodiment, the disposable sheath 70 may be constructed to include slits between the segments to increase the deformability of the sheath 70. The segments may be arranged into a geometry resembling a flower petal arrangement, fastened together at one end, such as near the aperture, for ease of installation. Preferably the sheath 70 is constructed from a flexible removable material such as rubber, plastic, fluoropolymer or other polymer, so that it may be economically provided as a disposable one time use piece. Example materials include nylon, polyphenyl sulfone, polyarylamide, polyvinylchloride, polyethylene, polypropylene, PTFE, PET, PFA and PEEK™. The material is chosen so that it will maintain its position relative to the ultrasound tip during use, but may be easily replaced after each use. The material needs to exhibit sufficient elasticity to stretch over the ultrasound tip 50 geometry during installation, while maintaining secure contact and conforming to the ultrasound tip during use.

Figure 2:
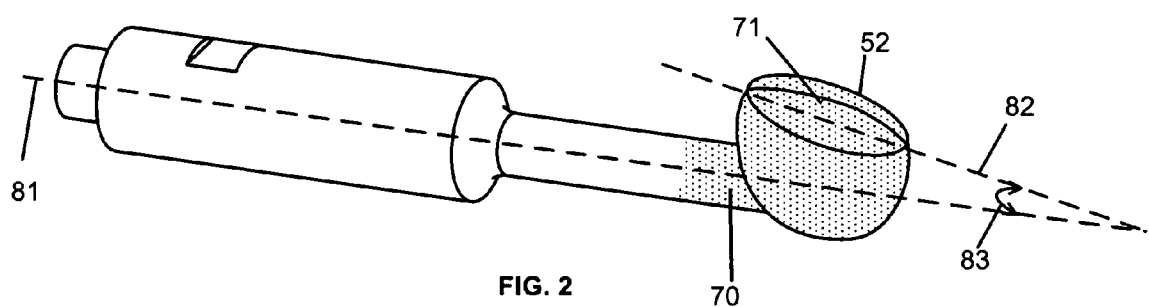
FIG. 2 depicts a perspective view on an embodiment of the medical apparatus with a permanent reusable sheath coating.

Alternatively, as shown in FIG. 2 the sheath 70 may be a reusable permanent polymer coating, chemically or physically bonded to the ultrasound tip 50 such as a fluoropolymer, epoxy or a plastic polymer that is integral with the tip and cleaned after each use. In this embodiment, the sheath 70 may be extremely thin for example, less than 1 mm, and utilize the structural strength of the metal tip for its support. Examples coating materials include nylon, polyethylene, parylene, PTFE, KYNAR™, HALAR™ and XYLAN™ among others.

FIG. 2 also shows the ultrasound horn 30 longitudinal axis 81 may be positioned to create an angle α 83 with the longitudinal aperture axis 82 of the sheath 70. The angle α 83 may vary between 0 and 180 degrees. Preferably the angle α 83 may vary from approximately 0 to 45 degrees.

Ultrasound may be applied to the skin and underlying tissues by at least two mechanisms. The sheath 70 may be contacted directly to the skin allowing ultrasound energy to be transferred directly from the device, for example, from a radial edge 52. Since the radial edge 52 is isolated from contacting the patient's skin, the radial edge 52 may be sharp, jagged, flat or rounded as desired to modify the ultrasound waves transmission and associated points of concentration of the ultrasound energy transmitted from the radial edge 52. In addition, the ultrasound energy may also be focused by the cavity 53 of the radial surface 51 to the skin. In doing this, the cavity 53 may focus the ultrasound energy with the coupling fluid 60 serving as a medium to allow transfer of the ultrasound waves to the skin surface. Typically, the focus of the cavity 53 is external to the cavity 53, at or below the skin layer so that the therapeutic effect of the ultrasound is directed to destroying the spider vein vascular tissue just below the skin surface. Coupling fluid 60 may also serve to transmit ultrasound energy from the radial edge 52 in those embodiments having the sheath 70 positioned to provide space between the radial edge 52 and the patient's skin leaving at least portions of the radial edge uncovered.

Coupling fluid 60 tends to facilitate the transmission of ultrasonic energy from the walls of the cavity 53 to skin and/or tissue to be treated. The cavity 53 may be at least partially filled with a coupling fluid 60 capable of conducting ultrasonic vibrations. The coupling fluid 60 may include, but not limited to, saline, water, alcohol, corn oil, vegetable oil, or any combination thereof. When the tip is ultrasonically vibrated, cavitations may form within the coupling fluid 60 or tissue. Additionally or in the alternative, the coupling fluid 60 within the cavity 53 may be atomized into a spray.

If a piezoelectric transducer is used to induce the substructure formed by the ultrasound horn 30, then the voltage of the electrical signal driving the transducer will largely control the degree to which the coupling fluid 60 is cavitated and/or atomized. At low voltages, the coupling fluid 60 within the cavity 53 will be cavitated to a small degree. As the voltage increases, the amount of cavitations within the coupling fluid 60 is increased. Further increasing the voltage will eventually induce atomization of the coupling fluid 60. Regardless of whether the coupling fluid 60 within the cavity 53 is quiescent, atomized and/or cavitated, the presence of a coupling fluid 60 within the cavity 53 may couple the transmission of ultrasonic energy released from the walls of the cavity 53 to the skin and/or tissue to be treated. The cavity 53 may be given an initial fill of coupling fluid 60 prior to its use. Alternatively, the coupling fluid 60 may be continuously provided to the cavity 53 by gravity or a pump to the ultrasound tip 50 through channel 44 to the cavity 53.

Coupling fluid 60 may flow along the surface of the cavity wall. Alternatively, coupling fluid 60 may leave the orifice and travel through the interior of the cavity 53 as a stream without contacting the cavity wall. Furthermore, the coupling fluid 60 may be reflected off the cavity wall and dispersed within the cavity 53. It is possible that coupling fluid 60 may be aspirated so that at least a portion is removed from the cavity 53. In any of the above alternatives the coupling fluid 60 is being directed towards the focal point(s) of the cavity 53. In addition to directing coupling fluid 60 towards the focal point of cavity 53, coupling fluid 60 may be transformed into a spray by the ultrasound energy being emitted from the interior of the cavity 53. The ultrasound waves released from the interior of the cavity 53 tend to push the spray in the direction the ultrasound waves are traveling. This direction is generally orthogonal to the surface of the cavity wall which is primarily transverse to the longitudinal axis 81 along the shaft 40 of the ultrasound horn 30. As such, the spray is directed by the ultrasound waves to the focal point of cavity 53. The ultrasonic energy carried with the coupling fluid 60 allows ultrasound waves and corresponding energy to be transferred to the skin surface, avoiding the relatively inefficient transmission of ultrasound energy through air. The coupling fluid 60 itself may also be used to provide a therapeutic effect at the skin surface.

The coupling fluid 60 may also contain a therapeutic agent to enhance treatment for specific applications. An integral return passage 72 may be included in the ultrasound tip 50, with the sheath 70, or between the sheath 70 and the ultrasound tip 50 to serve as a component to aspirate coupling fluid 60 away from the patient as it is being used.

Figure 3:
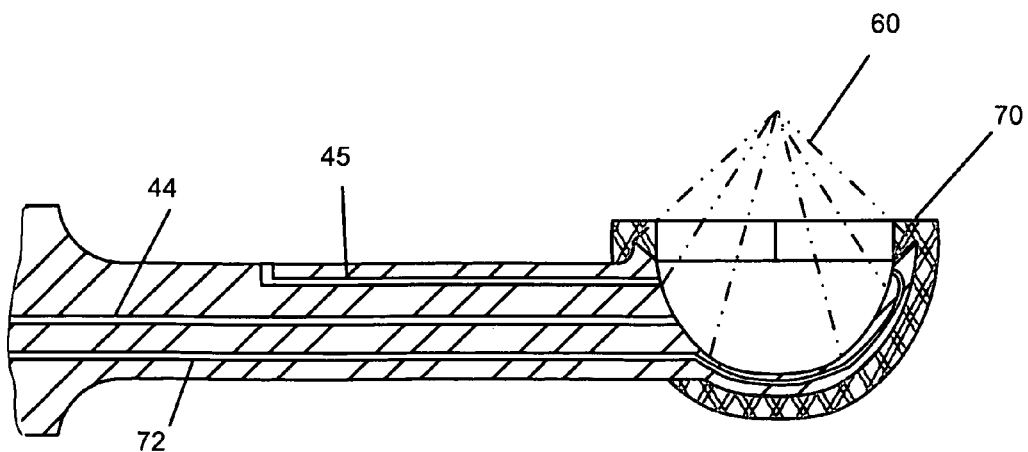
FIG. 3 depicts a cross sectional view of an embodiment of the ultrasound horn.

As shown in FIG. 3, the ultrasound tip 50 may include a return passage 72 in some embodiments. The return passage 72 may be within the ultrasound tip 50, between the sheath 70 and the ultrasound tip 50 or within the sheath 70. The return passage 72 may remove coupling fluid 60, tissue and other materials and fluids in the incision site and/or the cavity 53. The return passage 72 preferably connects between the ultrasound tip distal end and a vacuum source or aspirator.

Figure 4:
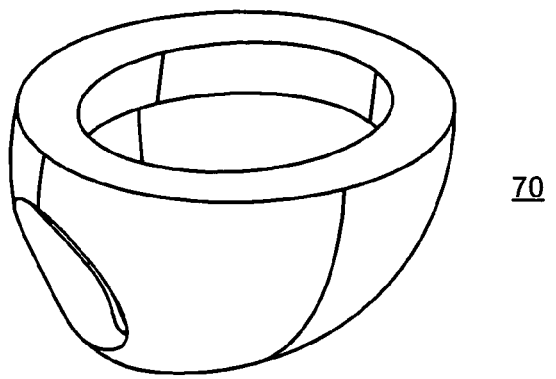
FIG. 4 depicts an embodiment of a disposable sheath.

In FIG. 4, a sheath 70 embodiment is shown that when installed would substantially surround the exterior surface of the ultrasound tip 50 parabolic surface with an aperture 71 external to the cavity 53 so that coupling fluid 60 may contact the patient's skin. Also shown is the segments of sheath 70 which may be only attached at portions of the adjacent segment such as near the sheath aperture.

Figure 5:
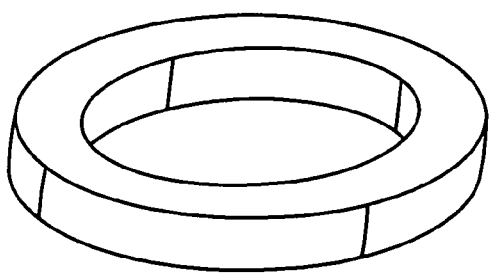
FIG. 5 depicts an alternative embodiment of a disposable sheath.

The FIG. 5 embodiment is directed to a sheath 70 that primarily covers the ultrasound tip 50 radial edge 52 allowing significant portions of the radial surface 51 to be uncovered by the sheath 70.

Figure 6:
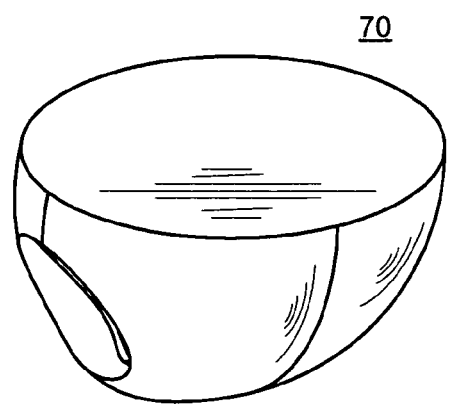
FIG. 6 depicts an alternative embodiment of a disposable sheath without an aperture.

FIG. 6 shows an embodiment having the cavity 53 completely covered with the sheath 70 which allows maintaining substantially all of the coupling fluid 60 within the cavity 53. In this embodiment, the cavity 53 focuses the ultrasound energy, which is transmitted through the coupling fluid 60. However, the coupling fluid 60 does not contact patient skin and substantially all ultrasound energy passes through the sheath 70 prior to reaching the patient.

As also shown in FIG. 3 the ultrasound tip 50 receives a coupling fluid 60, typically through a channel 44. Channel 44 may enter the ultrasound tip 50 longitudinally through the ultrasound transducer 20, shaft 40 and/or handle. An additional channel 45 may be included to transfer fluid such as a therapeutic agent or cryogenic fluid to or from the ultrasound tip 50. The coupling fluid 60 may also be delivered radially through means external to the device.

The ultrasonic energy and/or the waves carrying it may elicit a change in the membrane permeability of deep cellular structures such as, but not limited to, axons and somas, decreasing the sensation of pain in the treated area. Additionally or in combination, the mechanical energy generated by directing ultrasound waves towards a focal point may interact with nerve cells as to provide an analgesic effect.

The cavitation of coupling fluid 60, as well as the mechanical energy associated with the focused ultrasound energy can be used to assist the production of ozone from the oxygen associated with the air and/or liquid. The ozone produced may be utilized to assist the ultrasound energy to disrupt cellular materials and inactive pathogens. Thereby, the ozone may provide therapeutic disinfecting properties to help the patient resist infections.

Although specific embodiments of apparatuses and methods using the treatment of spider veins as an example, have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive. Combinations of the above embodiments and other embodiments as wells as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. A method to treat spider veins comprising the steps of:
   a. providing an apparatus comprising:
      i. a shaft containing a proximal end opposite a distal end, at least one radial surface extending between the proximal end and the distal end, and a longitudinal axis extending through the shaft from the proximal end to the distal end;
      ii. a tip attached to the distal end of the shaft containing at least one radial surface, a paraboloid cavity containing at least one wall and an opening within at least one of the radial surfaces of the tip wherein the plane of the opening is not orientated orthogonal to the longitudinal axis of the shaft;
      iii. a tapered structure at the opening of the cavity; and
      iv. a non-metallic sheath adjoined to the tip preventing the tapered structure at the opening of the cavity of the tip from contacting a patient's skin;
   b. collapsing a blood vessel by delivering ultrasound energy concentrated by a tapered structure directly to the skin of a patient; and
   c. disrupting the blood vessel by transmitting ultrasound energy focused towards a treatment area containing the blood vessel.

2. The method according to claim 1 further comprising, transferring a coupling fluid to the cavity of the tip.

3. The method according to claim 2 further comprising, inducing cavitations within the coupling fluid with the ultrasound energy focused towards the treatment area.

4. The method according to claim 2 further comprising, atomizing the coupling fluid with the ultrasound energy focused towards the treatment area.

5. The method of claim 2 wherein the ultrasound energy is transmitted by the combination of direct contact of the sheathed tapered structure and through the coupling fluid.

6. The method of claim 2 wherein the ultrasound energy focused towards the treatment area is transmitted by the coupling fluid.

7. The method of claim 2 wherein the coupling fluid includes a therapeutic agent.

8. The method according to claim 1 wherein the ultrasound energy is modulated.

9. The method according to claim 1 wherein the ultrasound energy is carried by vibrations at a frequency between approximately 15 kHz and approximately 3 mHz.

10. The method according to claim 1 wherein the ultrasound energy is carried by vibrations frequency of approximately 30 kHz.

11. The method according to claim 1 wherein the amplitude of the vibrations carrying the ultrasound energy being between approximately 1 micron and approximately 100 microns.

12. The method according to claim 1 wherein the amplitude of the vibrations carrying the ultrasound energy being approximately 80 microns.

13. The method of claim 1 wherein the ultrasound energy is transmitted by direct contact between the sheath and a patient.

* * * * *